United States Patent [19]

Backensfeld et al.

[11] Patent Number: 5,798,338
[45] Date of Patent: Aug. 25, 1998

[54] SOLID DOSAGE FORMS THAT CONTAIN CLATHRATES OF 17α-ETHINYL ESTRADIOL

[75] Inventors: Thomas Backensfeld; Johannes Tack, both of Berlin, Germany

[73] Assignee: Schering Aktiengesellschaft, Berlin, Germany

[21] Appl. No.: 765,823

[22] PCT Filed: Jul. 10, 1995

[86] PCT No.: PCT/EP95/02656

§ 371 Date: Apr. 2, 1997

§ 102(e) Date: Apr. 2, 1997

[87] PCT Pub. No.: WO96/02277

PCT Pub. Date: Feb. 1, 1996

[30] Foreign Application Priority Data

Jul. 20, 1994 [DE] Germany .................. 44 26 709.6

[51] Int. Cl.$^6$ .................. A61K 31/705; A61K 31/565
[52] U.S. Cl. .................. 514/26; 514/58; 514/182
[58] Field of Search .................. 514/58, 182, 26

[56] References Cited

U.S. PATENT DOCUMENTS 4,877,774  10/1989  Pitha et al. .................. 514/26

OTHER PUBLICATIONS

Pitha et al., Int. J. Pharm., 29(1), 73–82 (1986).

*Primary Examiner*—Phyllis Spivack
*Attorney, Agent, or Firm*—Millen, White, Zelano, & Branigan, P.C.

[57] ABSTRACT

A method and pharmaceutical compositions are disclosed for reducing oxidative degradation of 17 α-ethinylestradiol comprising combining the estradiol with an effective amount of cyclodextrin, thus forming a cyclodextrin clathrate of the steroid.

14 Claims, No Drawings

SOLID DOSAGE FORMS THAT CONTAIN CLATHRATES OF 17α-ETHINYL ESTRADIOL

The invention relates to solid dosage forms that contain steroidal sex hormones.

As is generally known, natural and especially synthetically derived sex hormones are generally highly effective active ingredients of pharmaceutical agents. Consequently, in most cases solid dosage forms contain these active ingredients at very low dosages; these are usually 0.01 μg to 500 μg and especially 0.1 μg to 200 μg per single-dosed dosage form. This means that both the preparation and the storage and use of these dosage forms are often problematical in nature.

In the preparation of such low-dosed dosage forms, strong fluctuations of the active ingredient concentrations in the dosage units occur almost unavoidably (inadequate content uniformity), which manifest themselves more strongly, the smaller the amount of the active ingredient.

In the storage of such low-dosed preparations, moreover, a reduction in the active ingredient concentration is often additionally observed as a result of, in most cases, oxidative degradation reactions of the active ingredient.

In addition, at such low dosage the bioavailability of the active ingredient is subject to a pronounced first-pass effect and exhibits great inter- and intra-individual fluctuations.

It has now been found that the drawbacks that are observed especially in the preparation and storage of dosage forms which contain low-dosed steroidal sex hormones can be avoided, at least to a large extent, if dosage forms are prepared that contain powdery cyclodextrin clathrates of these active ingredients.

Steroidal sex hormones that are suitable for the production of dosage forms according to the invention are estrogenically, gestagenically, androgen-anabolically, antiestrogenically, antigestagenically, and antiandrogenically active compounds, as well as mixtures of these substances.

For example, estrone, estradiol, estriol, 17α-ethinylestradiol, mestranol, 14α,17α-ethanoestra-1,3,5(10)-triene-3,17β-diol (WO88/01275), 14α,17α-ethanoestra-1,3,5(10)-triene-3,16α,17β-triol (WO and their esters such as estradiol-dipropionate, estradiol-dihexanoate and estradiol-didecanoate (EP-A 163 596) can be mentioned as examples of suitable estrogens.

Suitable gestagens are, for example, norethisterone, levonorgestrel, gestodene, desorgestrel, and 3-ketodesorgestrel.

Suitable androgen-anabolically active compounds are, i.a., testosterone, mesterolone, methenolone, and esters of these substances, such as testosterone propionate, testosterone enanthate, testosterone nicotinate, and testosterone phenylacetate.

Suitable antiestrogens are, i.a., 1-methyl-androsta-1,4-diene-3,17-dione (atamestane) and 7α-[9-[(4,4,5,5,5-pentafluoropentyl)-sulfinyl]-nonyl]estra-1,3,5(10)-triene-3,17β-diol (ICI 182780).

As suitable antigestagens, 11β-[4-(dimethylamino)-phenyl]-17β-hydroxy-17α-(3-hydroxypropyl)-13α-estra-4,9-dien-3-one (onapristone) and 11β-[4-dimethylamide-phenyl]-17β-hydroxy-17α-(1-propynyl)-estra-4,9-dien-3-one (mifepristone) can be mentioned.

Antiandrogenically active compounds that are suitable for the production of dosage forms according to the invention are, for example, 17α-acetoxy-6-chloro-pregna-4,6-diene-3,20-dione (chloromadinone acetate), 17α-acetoxy-6-chloro-1β,2β-dihydro-3H-cyclopropa[1,2]-pregna-1,4,6-triene-3,20-diene (cyproterone acetate) (topterone) and 17β-hydroxy-1α-methyl-17α-propyl-androstan-3-one (propylmesterolone).

It was already mentioned that the dosage forms according to the invention contain powdery cyclodextrin clathrates of these active ingredients.

Cyclodextrins that are suitable for the production of these clathrates are, for example, those of general formula

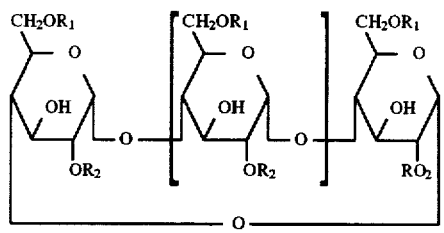

in which
R$_1$ means a hydrogen atom, a methyl group, a 2-hydroxyethyl group, or a 2-hydroxypropyl group
R$_2$ means a hydrogen atom or, if R$_1$ represents a methyl group, also a methyl group, and
n means a number from 4 to 7.

Such cyclodextrins are preferably α-cyclodextrin, γ-cyclodextrin, dimethyl-β-cyclodextrin, 2-hydroxyethyl-β-cyclodextrin, 2-hydroxypropyl-β-cyclodextrin and especially β-cyclodextrin (Drug Dev. and Ind. Pharm., 17, 1991, 1503–1549, J. Incl. Phenom., 1, 1983, 135–150 and WO 93/13138). For the production of clathrates, the steroid hormones can be very intimately mixed with the cyclodextrin, optionally with the addition of other pharmaceutical adjuvants (for example by stirring, kneading), or the solvent can be removed from a solution of the components in water and/or a suitable solvent (such as, for example, a C1–C4 alcohol such as methanol, ethanol or isopropanol or a C$_2$–C$_4$ ketone such as acetone or methyl ethyl ketone) by, for example, vacuum distillation, freeze-drying, or spray-drying. By contrast, it is also possible, however, to feed the steroid hormone that is dissolved in a suitable solvent (such as, for example, one of the above-mentioned alcohols or ketone) into an aqueous cyclodextrin solution, and to filter off and dry the precipitated clathrate.

Just like the active ingredients themselves, the clathrates can then also optionally be processed into the desired dosage forms, such as tablets, powder, granulates, etc. after the addition of the commonly used additives, such as, for example, lactose, starch, polyvinylpyrrolidone, magnesium stearate, and preservatives.

It is obvious to one skilled in the art that several common preliminary tests are required to determine what cyclodextrin is optimally suited for inclusion of the desired steroidal steroid hormone. In the case of very small steroid molecules, the use of α-cyclodextrin may be optimum, while in the case of inclusion of quite large steroid molecules, it may be necessary to use γ- or even δ-cyclodextrin as a host molecule. Normally, the ratio of cyclodextrin to steroid hormone is selected such that 1:1 mol:mol complexes are formed, which does not rule out the possibility, however, that in individual cases it may be more advantageous to select the molar ratio such that, for example, 2:1, 3:1, 3:2 or 1:2 complexes are formed.

The embodiments below are used for a more detailed explanation of the invention:

EXAMPLE 1

20.96 g of 17α-ethinylestradiol is dissolved in 20 ml of ethanol. 28.38 g of β-cyclodextrin (relative to anhydrous β-cyclodextrin) is dissolved in 900 ml of water while being stirred at 45° C. The ethanolic ethinylestradiol solution is added in drops to aqueous cyclodextrin solution within 40 minutes while being stirred, so that a slightly cloudy solution develops. Within 2 hours, the solution is cooled to 25° C. It is stirred for another 20 hours to 25° C. The precipitated solid is suctioned off and washed twice with 50 ml of water each. The crystallizate is suspended twice with 40 ml of acetone each and suctioned off. Then, it is rewashed with 50 ml of water. The wet crystallizate is dried in a vacuum with phosphorous pentoxide.

The content of 17α-ethinylestradiol in the inclusion bond is determined by means of high-pressure liquid chromatography and is 10.2%.

EXAMPLE 2

2.37 g of β-cyclodextrin is dissolved in 200 ml of water. 118.6 mg of 17α-ethinylestradiol is weighed into the aqueous cyclodextrin solution. The suspension is stirred for 48 hours. The solid is suctioned off and washed twice with 25 ml of water each. The crystallizate is suspended twice with 20 ml of acetone each and suctioned off. Then, it is rewashed with 20 ml of water. The wet crystallizate is dried in a vacuum with phosphorous pentoxide.

The content of ethinylestradiol in the inclusion bond is determined by means of high-pressure liquid chromatography and is 10.4%.

EXAMPLE 3

A β-cyclodextrin inclusion complex (produced according to Example 1) is ground and triturated in portions with lactose. Corn starch and modified starch are mixed in. The powder is processed into a granulate in a fluidized-bed granulator with an aqueous polyvinylpyrrolidone 25000 solution. After magnesium stearate is mixed in, the press dust that is obtained is pressed into tablets with a weight of 55 mg and a diameter of 5 mm.

| Composition of a Tablet: | |
| --- | --- |
| Ethinylestradiol/β-cyclodextrin inclusion compound ≡ 10 μg of 17α-ethinyl-estradiol | 0.098 mg |
| lactose | 35.102 mg |
| corn starch | 9.900 mg |
| modified starch | 6.600 mg |
| polyvinylpyrrolidone 25000 | 2.750 mg |
| magnesium stearate | 0.550 mg |
| | 55.000 mg |

EXAMPLE 4

A β-cyclodextrin inclusion complex (produced according to Example 2) is ground. 9.615 g of the complex (corresponding to 1 g of ethinylestradiol) is homogeneously added to a powder mixture that consists of 2360.385 g of lactose, 1300 g of microcrystalline cellulose, and 310 mg of corn starch. After 20 g of magnesium stearate is added, the powder press dust that is obtained is pressed with a tablet press into tablets with a 6 mm diameter and a tablet weight of 80 mg. They come with an active ingredient content of 20 μg of ethinylestradiol per tablet.

We claim:

1. A pharmaceutical composition comprising an effective amount of 17α-ethinylestradiol, and an amount of a β-cyclodextrin which is effective in reducing the oxidative degradation of the 17α-ethinylestradiol, wherein the composition is a clathrate.

2. A composition of claim 1, wherein the composition comprises about 10% w/w of 17α-ethinylestradiol to β-cyclodextrin.

3. A composition of claim 1, wherein the amount of 17α-ethinylestradiol is 0.01 μg–200 μg.

4. A composition of claim 1, wherein the amount of 17α-ethinylestradiol is 0.1 μg–200 μg.

5. A composition of claim 1, wherein the amount of 17α-ethinylestradiol is 10 μg–20 μg.

6. A composition of claim 1, wherein the 17α-ethinylestradiol is an inclusion in the β-cyclodextrin.

7. A method of reducing oxidative degradation of 17 α-ethinylestradiol comprising combining an amount of 17 α-ethinylestradiol and an amount of β-cyclodextrin which is effective in reducing the oxidative degradation of said estradiol.

8. The method of claim 7, wherein the 17 α-ethinylestradiol and the β-cyclodextrin are in a 1:1 mole:mole ratio.

9. The method of claim 7, wherein the amount of 17 α-ethinylestradiol is 0.01 μg–200 μg.

10. The method of claim 7, wherein the amount of 17 α-ethinylestradiol is 0.1 μg–200 μg.

11. A method of making a pharmaceutical composition, comprising an effective amount of 17α-ethinylestradiol and an amount of a β-cyclodextrin which is effective in reducing the oxidative degradation of the 17α-ethinylestradiol, wherein the composition is in a solid dosage form, comprising, combining an amount of 17 α-ethinylestradiol and an amount of β-cyclodextrin which is effective in reducing the oxidative degradation of said estradiol.

12. The method of claim 11, further comprising dissolving the 17 α-ethinylestradiol in a suitable solvent, dissolving the β-cyclodextrin in an aqueous solution, combining said solutions of 17 α-ethinylestradiol and β-cyclodextrin, and isolating the resulting precipitated clathrate.

13. The method of claim 11, further comprising dissolving the β-cyclodextrin in an aqueous solution, adding solid 17 α-ethinylestradiol to said aqueous solution, and isolating the resulting clathrate.

14. A method of achieving an estrogenic effect comprising, administering a pharmaceutical composition, comprising an effective amount of 17α-ethinylestradiol and an amount of β-cyclodextrin which is effective in reducing the oxidative degradation of the 17α-ethinylestradiol, wherein the composition is in a solid dosage form.

* * * * *